(12) United States Patent
Voigt et al.

(10) Patent No.: US 12,369,989 B2
(45) Date of Patent: Jul. 29, 2025

(54) MEDICAL APPARATUS FOR DETERMINING THE RELATIVE SPATIAL POSITION OF A PLANAR MARKER

(71) Applicant: Carl Zeiss Meditec AG, Jena (DE)

(72) Inventors: Christian Voigt, Abtsgmuend (DE); Nils Haverkamp, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 519 days.

(21) Appl. No.: 17/705,238

(22) Filed: Mar. 25, 2022

(65) Prior Publication Data

US 2022/0304754 A1 Sep. 29, 2022

(30) Foreign Application Priority Data

Mar. 25, 2021 (DE) .................... 10 2021 202 951.5

(51) Int. Cl.
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2055* (2016.02); *A61B 2090/3937* (2016.02)

(58) Field of Classification Search
CPC ............ A61B 90/39; A61B 2034/2055; A61B 2090/3937; A61B 2090/3983; A61B 2034/2065; A61B 2034/2068; A61B 90/20

See application file for complete search history.

(56) References Cited

U.S. PATENT DOCUMENTS

| | | | | |
|---|---|---|---|---|
| 5,038,258 | A | * | 8/1991 | Koch .................... G01J 3/10 362/237 |
| 8,988,505 | B2 | * | 3/2015 | Schaerer ............... A61B 90/96 348/46 |
| 10,314,490 | B2 | * | 6/2019 | Ntziachristos ....... A61B 5/0095 |
| 2002/0040190 | A1 | * | 4/2002 | Nagele ................. A61B 90/20 600/476 |
| 2008/0103390 | A1 | * | 5/2008 | Contag ................. A61B 90/36 600/478 |
| 2016/0228198 | A1 | * | 8/2016 | Hong .................... A61B 90/39 |
| 2017/0143442 | A1 | * | 5/2017 | Tesar .................... A61B 90/37 |
| 2019/0328464 | A1 | * | 10/2019 | Saur .................... G02B 21/0012 |
| 2020/0138518 | A1 | * | 5/2020 | Lang .................... A61B 90/37 |

OTHER PUBLICATIONS

Office Action issued in German Patent Application No. DE 10 2021 202 951.5, dated Nov. 25, 2021 (from which this application claims priority) and English language translation thereof.

* cited by examiner

*Primary Examiner* — Carl H Layno
*Assistant Examiner* — Bryan McAllister Lee
(74) *Attorney, Agent, or Firm* — Ewers IP Law PLLC; Falk Ewers

(57) ABSTRACT

A medical apparatus for determining a relative spatial position of a planar marker is provided. The medical apparatus has an illumination device configured to illuminate the marker, a detector configured to detect light steered from the marker to the detector, and an evaluation device configured to determine a direction of a tilt of the marker from an analysis of a first value detected by the detector while the marker is illuminated from a first direction and a second value detected by the detector while the marker is illuminated from a second direction.

18 Claims, 5 Drawing Sheets

MEDICAL APPARATUS FOR DETERMINING THE RELATIVE SPATIAL POSITION OF A PLANAR MARKER

CROSS REFERENCE TO RELATED APPLICATIONS

This application claims priority to German patent application DE 10 2021 202 951.5, filed Mar. 25, 2021, the entire content of which is incorporated herein by reference.

TECHNICAL FIELD

The disclosure relates to a medical apparatus for determining the relative spatial position of a planar marker within the scope of a medical examination or a medical intervention. Furthermore, the disclosure relates to a system of a planar marker and such a medical apparatus, and to a method for determining the relative spatial position of a marker.

BACKGROUND

Within the scope of a medical examination or a medical intervention it may be helpful or even necessary to determine the relative spatial position of an object, that is to say the position and orientation of the object. By way of example, the determined relative position information may be input into the controller of robotic stands for imaging apparatuses, for which knowledge of the relative spatial position of the patient relative to the image sensor system of the apparatus is required. In the field of surgery there also is an increasing need for apparatuses for detecting the relative spatial position of an object. These apparatuses are used for the performance and/or for the documentation of surgical interventions. An example of such an application is the tracking for intraoperative navigation.

In many cases, markers which can be detected by a detection apparatus are attached to the object for the purposes of implementing the determination of the relative position. Small balls that reflect light in the infrared range are frequently used as markers. Since these balls in each case supply only position information and no angle information, a plurality of balls attached to different points on the object are required for a complete determination of the relative spatial position. This drives up the costs and may lead to problems, for example in the case of small objects or in the case of objects which do not have space for markers of this form for other reasons. Moreover, the detection of markers of this form requires comparatively much outlay in terms of apparatus.

Planar markers where only one marker is required per object for the purposes of performing the determination of the relative position are also already known. As a rule, the outlay in terms of apparatus for the detection of these planar markers is lower than for markers in the form of balls. However, examinations by the inventors have yielded that measurement artefacts may occur under certain circumstances if planar markers are used.

If a single camera is used for the detection of the planar marker and the marker is tilted such that the marker includes a small angle with a plane oriented perpendicular to the optical axis of the camera, then difficulties may occur in the determination of the sign of the tilt. Below, a tilt is considered to be an orientation where the marker is not aligned perpendicular to the optical axis of the camera. What may happen is that the wrong sign and hence a tilt in the wrong direction is determined. As a result of the noise in the measurement signals there may also be continual jumping between a positive and negative sign of the determined tilt angle and hence an alternating determination of a tilt in one direction and in the opposite direction thereto. Possible errors when determining the sign of the tilt angle of the marker have as a consequence corresponding errors in the determined relative position of the object to which the marker has been attached.

However, when determining a relative position in the field of medicine, great importance as a rule is placed not only on high precision but also on a low probability of a malfunction so as to avoid the patient being harmed. Determining a wrong tilt direction of an object may have fatal consequences, and so the use of a planar marker can be risky within the scope of a medical examination or a medical intervention where small tilt angles of the marker may occur in relation to a plane perpendicular to the optical axis of the camera used to detect the marker. This problem needs to be taken into account when using markers used in planar fashion, which otherwise have a number of advantages, in medical interventions and medical examinations.

SUMMARY

It is therefore an object of the disclosure to facilitate a reliable detection of the relative spatial position of a planar marker within the scope of a medical examination or medical intervention.

This object is achieved by a medical apparatus, a method, and a system for determining a relative spatial position of a marker as described herein.

The medical apparatus according to an aspect of the disclosure for determining the relative spatial position of a planar marker has an illumination device for illuminating the marker and a detector for detecting light steered from the marker to the detector. Furthermore, the medical apparatus according to an aspect of the disclosure has an evaluation device for determining the direction of a tilt of the marker. The direction of the tilt is determined from an analysis of a first value detected by the detector while the marker is illuminated from a first direction and a second value detected by the detector while the marker is illuminated from a second direction.

Within the scope of the disclosure, a tilt of the marker is considered to be an orientation which does not result from pivoting the marker about the optical axis of the detector, and so a tilt is always present whenever the marker is not aligned at right angles to the optical axis of the detector. In particular, the angle and the direction of the tilt of the marker can be determined relative to a plane perpendicular to the optical axis of the detector.

An advantage of the disclosure is that it facilitates a reliable detection of the relative spatial position and, in particular, the direction of the tilt of a planar marker within the scope of a medical examination or a medical intervention. What is particularly advantageous is that this determination reliably succeeds even in the case of small tilt angles and for a large bandwidth of detector optical units, in particular for a large range of focal lengths. Accordingly, the detector optical unit can have a comparatively large focal length which, in turn, facilitates a relatively small marker and/or a detector with a comparatively low resolution.

Further advantages consist in the fact that the medical apparatus according to an aspect of the disclosure can have a simple structure, a compact form and a cost-effective realization. Moreover, the medical apparatus according to an aspect of the disclosure can be integrated into existing products without problems.

The detection of the first value may be synchronized with the illumination from the first direction and/or the detection of the second value may be synchronized with the illumination from the second direction. Furthermore, both values may be detected during a comparable, typically identical, operation of the detector. This ensures that the detected values are representative of the utilized light directions and are not falsified by other influences.

The analysis can be implemented by way of a comparison of the first and the second value. The first and second value can each be a value for the luminous intensity, or a quantity related therewith. Depending on the result of the analysis it is possible to deduce whether the marker faces the first or the second illumination direction more, and the direction of the tilt can be determined as a result. In particular, the direction of the tilt can be determined from the fact that the illumination direction for which the larger value of the luminous intensity was detected includes a smaller angle with a normal oriented perpendicular to the marker than the illumination direction for which the smaller value of the luminous intensity was detected.

The first direction and the second direction from which the marker is illuminated can be varied depending on the spatial orientation of a tilt axis about which the marker is tilted. In particular, the first and the second direction can be varied such that the marker is in each case illuminated in a manner that is as perpendicular to the tilt axis as possible. The advantage of this is that the difference between the two detected values is maximized and, as a result, the comparison of the values supplies a particularly reliable result and, accordingly, the direction of the tilt may also be determined with great reliability.

Furthermore, the arrangement according to an aspect of the disclosure may be formed such that the illumination of the marker is varied depending on the position of the marker. By way of example, the intensity of the light generated by the illumination device may be varied globally for both illumination directions or individually for each illumination direction. In particular, the illumination may be varied depending on the distance of the illumination device from the marker and/or depending on the distance between marker and detector. This can both ensure sufficient illumination at large distances and avoid overexposure at small distances. Furthermore, the illumination may be varied depending on the lateral displacement of the marker in relation to the optical axis of the detector. This can compensate a different illumination of the marker for the two illumination directions, which potentially accompanies such a displacement, and hence increase the reliability of the determination of the direction of the tilt.

Moreover, the illumination device can illuminate the marker using light at a different wavelength to the ambient light in the operational surroundings provided for the medical apparatus according to the disclosure. This is advantageous in that the medical apparatus according to an aspect of the disclosure is less failure-prone in relation to influences of the ambient light. In particular, a wavelength in the infrared range may be provided.

The illumination device can have a plurality of light sources and the illumination from the first direction can be realized by a first subset of light sources and the illumination from the second direction can be realized by a second subset of light sources. The first subset of light sources and the second subset of light sources may be arranged at different positions. This facilitates a realization of the illumination from different directions with comparatively little outlay.

The light sources can have at least in pairs an identical emission characteristic within a solid angle range provided for the illumination of the marker. This contributes to the illumination of the marker from the first and the second direction being implemented under the same conditions and has a positive effect on the reliability of the determination of the direction of the tilt.

Such an emission characteristic may already be formed within the scope of the light sources being manufactured. This may save subsequent calibration outlay, depending on the long-term stability. It is likewise possible for the light sources to be calibrated at least in pairs. In particular, a calibration mode may be provided in the medical apparatus according to an aspect of the disclosure, within the scope of which the light sources are calibrated at least in pairs with an orientation of the marker perpendicular to the optical axis, and so the calibration can be implemented according to requirements. In this way, an identical emission can be obtained over the entire service life of the medical apparatus according to an aspect of the disclosure. By way of example, within the calibration mode provision may be made for a respective value for the light steered from the marker to the detector to be detected for at least two light sources and for the brightness of at least one of these light sources to be adjusted such that the detected values are the same.

The light sources can have an isotropic emission characteristic within the solid angle range provided for the illumination of the marker. What this can achieve is that the illumination of the marker depends predominantly on the distance to the light source and depends less strongly on the relative positioning.

The first subset of light sources and the second subset of light sources can be switched on and off in complementary fashion for the purposes of switching between the illumination from the first direction and the illumination from the second direction. In this way, the illumination of the marker from different directions under respectively comparable conditions can be obtained with little outlay.

In one modification, all light sources can be permanently switched on and the light path of the second subset of light sources may be blocked for the illumination from the first direction and the light path of the first subset of light sources may be blocked for the illumination from the second direction. Depending on the design of the light sources, a longer service life and/or more uniform illumination conditions for both directions may be obtained by this modification since switching-related instabilities are avoided.

It is likewise also possible that the first subset of light sources emits light at a first wavelength and the second subset of the light sources emits light at a second wavelength. The first value can be detectable by detecting light at the first wavelength and the second value can be detectable by detecting light at the second wavelength.

Disadvantages due to switching can also be avoided in this variant. In principle, instead of the time-sequential detection in other variants, it is even possible to carry out a simultaneous detection of both illumination directions if the detector can distinguish between the wavelengths.

In a further variant, the illumination has a movable light source. In this variant, the light source is brought into a first position for the illumination from the first direction and brought into a second position for the illumination from the second direction. This is advantageous in that an identical emission characteristic is obtainable for both illumination directions without additional effort and, in particular, a calibration can be dispensed with.

The illumination device may have an even number of light sources. As a result, it is possible to evenly divide the light sources among the two illumination directions such that the observance of comparable illumination conditions for both illumination directions is made easier.

Furthermore, the illumination device may have more than two light sources. As a result, there is, independently of the orientation of the tilt axis of the marker, the possibility of avoiding the light for both illumination directions striking the marker at a similar angle of incidence and accordingly leading to similar detected values. Moreover, there is the chance that the marker is illuminated in each case in a manner that is as perpendicular to the tilt axis as possible and large differences in the detected values are obtained as a consequence of the maximized differences in the angle of incidence accompanying this. This in turn leads to a great reliability when determining the direction of the tilt.

The light sources can be arranged on a circle that is concentric with the optical axis of the detector. In particular, the light sources may be arranged equidistantly from one another. This assists in the creation of comparable conditions for the illumination of the marker from the two directions and therefore increases the reliability when determining the direction of the tilt.

The detector may be in the form of a camera. In particular, the medical apparatus according to an aspect of the disclosure may have exactly one detector in the form of a camera. An advantage thereof is that the outlay in terms of apparatus is very low. Moreover, the camera is generally present in any case for the conventional determination of relative position, and so no further camera or any other detector is required for determining the direction of the tilt. The camera may have a plurality of pixels and the first value and the second value can each be determined by averaging the signals of a plurality of pixels or by summating the signals of a plurality of pixels. This has the advantage of a high resolution and a high sensitivity. The evaluation device may be integrated in the detector. This facilitates a compact structure.

The medical apparatus may be in the form of a surgical microscope.

The disclosure further relates to a system of a planar marker and the medical apparatus according to a further aspect of the disclosure.

The marker may be produced from a web-like material. This facilitates an efficient and cost-effective production, especially for very flat markers as well. Furthermore, the marker may have a carrier. In particular, the marker may be in the form of a tag or a label.

The marker may have a geometric pattern. The pattern may be in a form that facilitates a very precise determination of the relative position. Information relating to the object to which the marker has been attached may also be encoded in the pattern. By way of example, the pattern may be in the form of a quick response (QR) code. The pattern may be applied to, for example printed on, a carrier. It is likewise also possible for the pattern to be designed for direct attachment to the object, for example by being printed on. This facilitates a particularly flat and cost-effective embodiment of the marker.

Furthermore, the disclosure relates to a method for determining the relative spatial position of a marker, in particular within the scope of a medical examination or a medical intervention, wherein a detector for detecting light steered from the marker to the detector is provided, the marker is illuminated from a first direction and a first value is detected by the detector in the process, the marker is illuminated from a second direction and a second value is detected by the detector in the process, and the direction of a tilt of the marker is determined from the first and second value.

BRIEF DESCRIPTION OF THE DRAWINGS

The disclosure will now be described with reference to the drawings wherein.

DESCRIPTION OF EXEMPLARY
EMBODIMENTS

Figure 1:
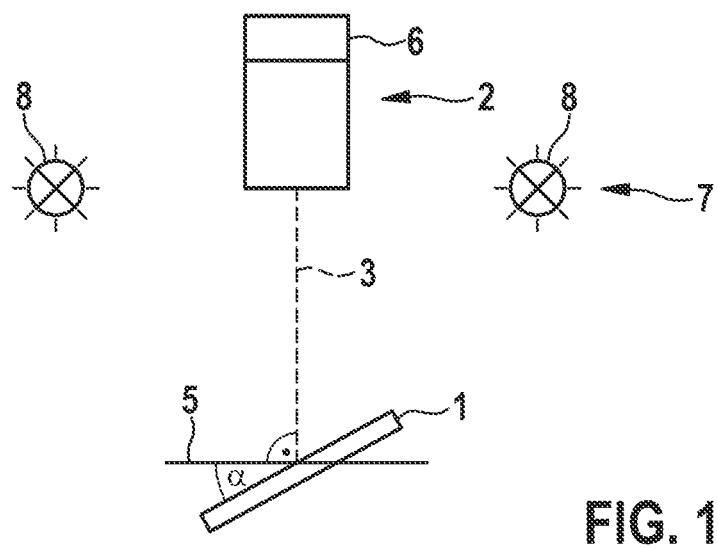
FIG. 1 shows a schematic side view of a system formed during a first operational state according to a first exemplary embodiment of the disclosure.
Figure 2:
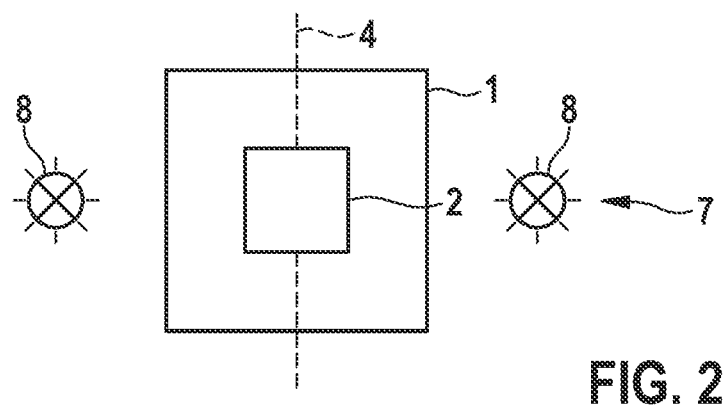
FIG. 2 shows a schematic plan view of the system during the first operational state according to the first exemplary embodiment of the disclosure.

FIG. 1 shows a schematic side view of a system during a first operational state according to a first exemplary embodiment of the disclosure. An associated schematic top view is depicted in FIG. 2.

The system has a planar marker 1, which can be attached to an object and the relative spatial position of which is of interest within the scope of a medical examination or medical intervention. The relative spatial position is understood to mean the spatial position and orientation. The relative spatial position can be represented by a combination of three spatial coordinates and three angle coordinates. Since the marker 1 is securely attached to the object, the relative spatial position of the object can be determined from the relative spatial position of the marker 1.

Furthermore, the system has a detector 2 which for example is in the form of a camera and has an optical axis 3. The detector 2 is arranged with a line-of-sight to the marker 1 such that light from the marker 1 can reach the detector 2. The marker 1 is tilted relative to the detector 2 with respect to a tilt axis 4. A tilt is present whenever the marker 1 is not oriented parallel to a plane 5 that is spanned perpendicular to the optical axis 3. An angle α between the marker 1 and the plane 5 specifies the size of the tilt.

An evaluation device 6 and an illumination device 7, which has two light sources 8, are provided as further components. As illustrated in FIG. 1, the evaluation device 6 may be integrated into the detector 2. Alternatively, the evaluation device 6 may also be in the form of a separate component. The light sources 8 are arranged diametrically opposite one another at the same distances from the optical axis 3 of the detector 2 and illuminate the marker 1. The evaluation device 6 can actuate the light sources 8 on an individual basis and put these into either a switched-on or a switched-off state. Both light sources 8 are switched on in the representation of FIG. 1.

Figure 3:
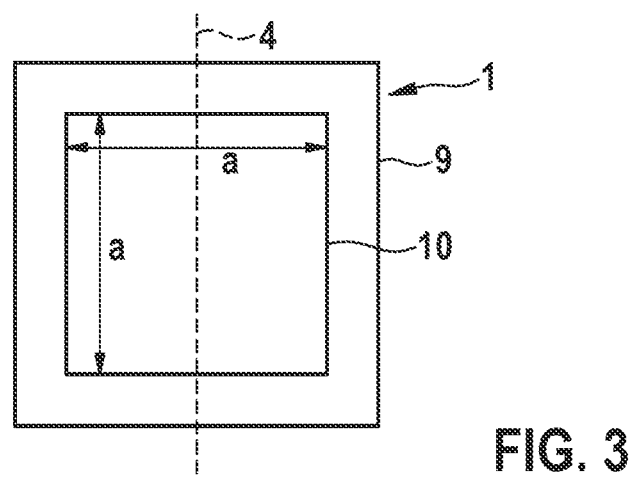
FIG. 3 shows a plan view of a possible exemplary embodiment of the marker.

The exemplary embodiment of the marker 1 is explained in more detail on the basis of FIG. 3.

FIG. 3 shows a plan view of a possible exemplary embodiment of the marker 1.

The marker 1 depicted in FIG. 3 has a carrier 9, to which a pattern 10 has been applied. In particular, the carrier 9 may be produced from a web-like material and for example be in the form of a plastic or metal film, in the form of a piece of paper or cardboard, etc. In particular, the carrier 9 may have a self-adhesive form and have an adhesive layer, with the aid of which the marker 1 can be fastened to the object.

For reasons of clarity, especially also in view of the subsequent description of the procedure when determining the relative spatial position of the marker 1, an exemplary embodiment was chosen for the representation of FIG. 3, in which the pattern 10 of the marker 1 is in the form of a square with four equally long sides of side length a. As a rule, the marker 1 will have a significantly more complex pattern 10, which may for example be in the form of a QR code, etc. However, this changes nothing in the basic procedure when determining the relative spatial position.

The pattern 10 may be printed onto the carrier 9 or attached in any other way. As an alternative to the exemplary embodiment of the marker 1 depicted in FIG. 3, it is for example also possible to omit the carrier 9 and print or otherwise apply the pattern 10 onto the object.

The following procedure may be followed to determine the relative spatial position of the marker 1 and hence also of the object to which the marker 1 has been attached:

Initially, in the first operational state, in which depending on the light conditions all light sources 8 are switched off or all light sources 8 are switched on, the relative spatial position of the marker 1 is determined by the evaluation device 6 by evaluating the image information of the marker 1 captured by the detector 2.

In this case, the determination of two of the three spatial coordinates of the marker 1 is based on the fact that a change in the position of the marker 1 relative to the detector 2 in a manner perpendicular to the optical axis 3 of the detector 2 leads to a change in the position in the image of the pattern 10 detected by the detector 2. Consequently, two of the three spatial coordinates of the marker 1 can be determined by the evaluation device 6 from the position of the image of the pattern 10 detected by the detector 2. These two spatial coordinates specify the position of the marker 1 in the plane 5 that is oriented perpendicular to the optical axis 3.

The determination of the third spatial coordinate of the marker 1 is based on the fact that a change in position of the marker 1 parallel to the optical axis 3 brings about a change in the size of the detected image of the pattern 10, that is to say the side length in the image of the square detected by the detector 2 changes depending on the distance of the marker 1 from the detector 2. However, this change is identical for all four sides of the square, and so all sides continue to be of the same length and the image detected by the detector 2 still is a square. From the side length of this square, the evaluation unit 6, with knowledge of the actual side length a of the pattern 10 and with knowledge of the optical properties of the detector 2, can determine the position of the marker 1 parallel to the optical axis 3 of the detector 2 and can consequently determine the third spatial coordinate of the marker 1.

A rotation of the marker 1 about the optical axis 3 of the detector 2 is expressed in a corresponding rotation of the image detected by the detector 2, and so the angular orientation of the image allows the evaluation device 6 to determine the associated rotational angle orientation of the marker 1, which corresponds to the first of the three angle coordinates.

The two other angle coordinates correspond to tilts of the marker 1 about a respective tilt axis 4, the tilt axes 4 being oriented perpendicular to one another and to the optical axis 3. The following explanations are based on a tilt only about the tilt axis 4 which runs vertically in the representation of FIGS. 2 and 3. The image of the marker 1 tilted about the tilt axis 4 according to FIG. 3, which is detected by the detector 2, is depicted in FIG. 4.

Figure 4:
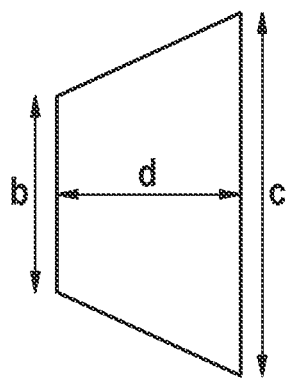
FIG. 4 shows an image, detected by the detector, of the marker according to FIG. 3.

FIG. 4 shows an image, detected by the detector 2, of the marker 1 according to FIG. 3.

The marker 1 is tilted about the tilt axis 4 that is oriented perpendicular to the optical axis 3 of the detector 2. In the representation of FIG. 4, the tilt axis 4 is oriented vertically and runs centrally through the pattern 10. As a result of the tilt of the marker 1, the detected image contains a perspective distortion of the pattern 10 in the form of a square. As a consequence of this distortion, a side of the square that is oriented parallel to the tilt axis 4 and arranged at a larger distance from the detector 2 as a result of the tilt appears compressed in the detected image and has a side length b in the representation of FIG. 4. The opposite side is arranged at a shorter distance from the detector 2 as a result of the tilt and therefore appears stretched in the recorded image, and has a side length c in the representation of FIG. 4. Accordingly, the side lengths b and c are not identical. Side length c is longer than side length b.

The tilt moreover causes the aforementioned opposing sides to be arranged at a shorter distance d from one another in the detected image than would be the case in the non-tilted state of the marker 1. Overall, a trapezium arises in the detected image as a result of the perspective distortion of the pattern 10 in the form of the square. The tilt angle α can be determined from the perspective distortion of the pattern 10. In this case, the absolute value of the tilt angle α emerges from the ratio of the distance d to the mean value of side lengths b and c. The direction of the tilt arises from a comparison of the side lengths b and c. Unlike the distance d determined from the detected image, the side lengths b and c determined from the detected image depend on the optical properties of the detector 2. The intention is to explain this on the basis of FIG. 5.

Figure 5:
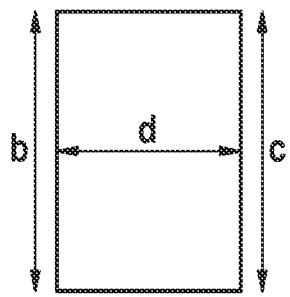
FIG. 5 shows a further image, detected by the detector, of the marker according to FIG. 3.

FIG. 5 shows a further image, detected by the detector 2, of the marker 1 according to FIG. 3.

When this image was recorded, the marker 1 was tilted in a manner identical to that in FIG. 4. However, the detector 2 used to detect the image depicted in FIG. 5 has different optical properties to the detector 2 used for the detection of the image according to FIG. 4. In particular, the detector 2 used in FIG. 5 differs in that it has a substantially longer focal length than the detector 2 according to FIG. 4. As a consequence, the difference in length between side lengths b and c is very small in FIG. 5 despite an identical tilt of the marker 1, and this difference may no longer be identifiable within the scope of measurement noise. This makes a reliable determination of the direction of the tilt difficult. In the absence of additional measures, the evaluation device 6 might even continually determine an alternating tilt direction. For this reason, further measures which facilitate a reliable determination of the tilt direction are made available within the scope of the disclosure. These measures include that, following the above-described determination of the absolute value of the tilt angle α, the light sources 8 are actuated by the evaluation device 6 in such a way that the one light source 8 is switched on and the other light source 8 is switched off. This situation is shown in FIG. 6.

Figure 6:
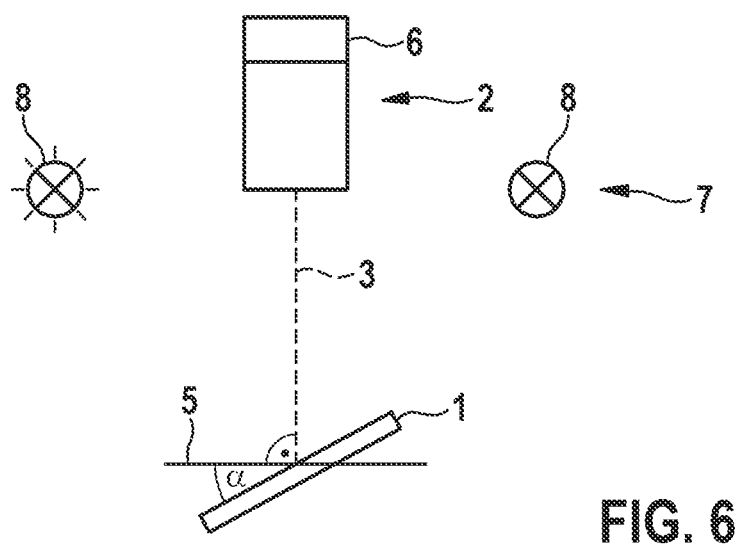
FIG. 6 shows a schematic side view of the system during a second operational state according to the first exemplary embodiment of the disclosure.

FIG. 6 shows a schematic side view of the system during a second operational state according to the first exemplary embodiment of the disclosure.

During the second operational state, the light sources 8 are actuated by the evaluation device 6 in such a way that the light source 8 depicted to the left in FIG. 6 is switched on and the light source 8 depicted to the right in FIG. 6 is switched off. Consequently, the marker 1 is only illuminated by the light of the switched-on light source 8 depicted to the left in FIG. 6, said light striking the marker 1 from a first direction, more precisely from a first range of directions. The detector 2 detects the intensity of the light of the switched-on light source 8, steered from the marker 1 to the detector 2. To this end, the detector 2 may be formed like a camera, as already described in the case of the first operational state, since as a rule a camera is able not only to detect an image but also to measure the intensity of the light generating this image. In this context, a particularly high resolution can be achieved by virtue of averaging over all pixels of the camera or summating the signals of all pixels. The determined intensity value is made available to the evaluation device 6 for the further analysis, that is to say the detector 2 supplies a signal dependent on the detected intensity to the evaluation device 6.

Instead of the above-described direct detection of the intensity, the intensity or a quantity related to the intensity may also be determined indirectly. By way of example, the luminous intensity incident on the detector 2 can be summated until a specified value is reached and the time that has elapsed until this value is reached can be used as a measure for the intensity of the light, and can be made available to the evaluation device 6.

Following the direct or indirect determination of intensity, a further measurement is carried out in a third operational state.

Figure 7:
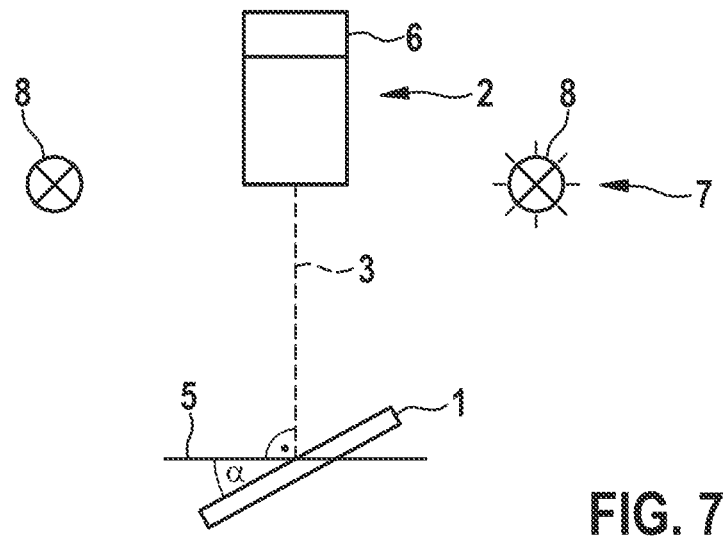
FIG. 7 shows a schematic side view of the system during a third operational state according to the first exemplary embodiment of the disclosure.

FIG. 7 shows a schematic side view of the system during a third operational state according to the first exemplary embodiment of the disclosure.

During the third operational state, the light sources 8 are actuated by the evaluation device 6 in such a way that the light source 8 depicted to the right in FIG. 7 is switched on and the light source 8 depicted to the left in FIG. 7 is switched off. Consequently, the marker 1 is only illuminated by the light of the switched-on light source 8 depicted to the right in FIG. 7, said light striking the marker 1 from a second direction, more precisely from a second range of directions. The detector 2 detects the intensity of the light of the switched-on light source 8, steered from the marker 1 to the detector 2, and makes the determined intensity value available to the evaluation device 6 for the further analysis, that is to say the detector 2 supplies a signal dependent on the detected intensity to the evaluation device 6. Alternatively, the intensity or a quantity related therewith may also be determined indirectly and a corresponding signal may be supplied to the evaluation device 6.

Overall, the detection of the luminous intensity by the detector 2 is synchronized with the control of the light sources 8, that is to say with the switching on and switching off of the light sources 8, and so the light of the desired light source 8 is detected in each case.

Figure 12:
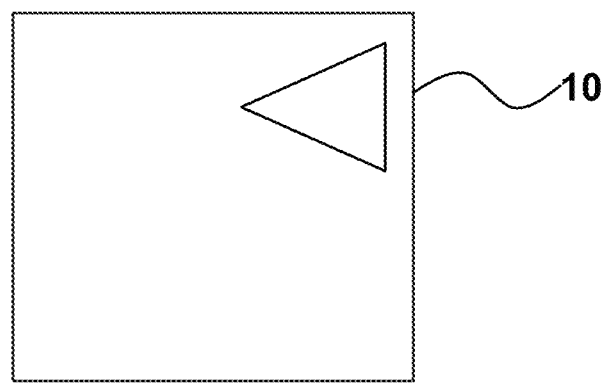
FIG. 12 shows a plan view of a geometric pattern of the planar marker according to an exemplary embodiment of the disclosure.

The evaluation device 6 analyses the intensity values detected during the second and during the third operational state. By way of example, the analysis is implemented by a comparison of the intensity values. As a rule, the marker 1 is tilted toward the light source 8 which was switched on during the detection of the larger of the two intensity values. In FIGS. 6 and 7, the marker 1 is in each case tilted toward the light source 8 depicted on the left. When this light source 8, toward which the marker 1 is tilted, is switched on, a larger component of the light is steered from the marker 1 to the detector 2 on account of the more advantageous geometry, as depicted in FIG. 12, than when the opposing light source 8, respectively depicted to the right in FIGS. 6 and 7, is switched on. Accordingly, a higher intensity being detected during the second operational state, which is depicted in FIG. 6, than during the third operational state, which is depicted in FIG. 7, is expected in the first exemplary embodiment since the marker 1 is tilted to the light source 8 depicted on the left in FIGS. 6 and 7 in the first exemplary embodiment and this light source is switched on during the second operational state. Consequently, the direction of the tilt arises from the analysis of the intensity values. The result does not jump between opposite directions. However, the analysis of the intensity values does not supply any quantitative results in respect of the tilt angle α. Therefore, the absolute value of the tilt angle α is determined as described above and the sign thereof is obtained following the analysis of the intensity values.

Since the sign of the tilt angle α is determined not from the perspective distortion but from an evaluation of the detected intensity during different illumination directions, a perspective distortion that is as large as possible need not be considered in relation to the optical properties of the detector 2. Other criteria may be taken into consideration instead, for example the desire for a long focal length in order to obtain high accuracy, especially in the case of a very distant marker 1. As a result, it is possible to use a small marker 1 and/or relax the requirements of the detector 2 in respect of resolution.

To reduce the susceptibility of the system according to an aspect of the disclosure to variations in the ambient light, there is the option of using light sources 8 which emit light at a wavelength that deviates from the wavelength of the ambient light and of using a detector 2 which is sensitive to the wavelength of the light sources 8 but not to the wavelength of the ambient light. By way of example, this wavelength may lie in the infrared range. Filters may be used, both when generating and when detecting light at a certain wavelength or in a certain wavelength range.

Since the determination of the direction of the tilt of the marker 1 is based on a comparison of the intensity of the light from various light sources 8 which is steered by the marker 1 to the detector 2, it is important that the light sources 8 illuminate the marker 1 with light of the same intensity and that the detection of the intensity is also implemented under otherwise identical conditions. By way of example, the same exposure times should be used when detecting the intensity. Possible autocorrection mechanisms should be deactivated. Moreover, the control of the light sources 8 should be synchronized precisely with the detection of the light steered from the marker 1 to the detector 2.

An identical illumination of the marker 1 by the two light sources 8 can be achieved by the following measures:

Use can be made of identical light sources 8 with low tolerances and good long-term stability. As a result, an identical illumination of the marker 1 using both light sources 8 can be achieved during the operation of the system according to an aspect of the disclosure without additional outlay.

There is also the option within the scope of the production of the system according to an aspect of the disclosure of carrying out a calibration of the light sources 8 at the factory. Additionally or as an alternative, such a calibration may be carried out prior to each start-up of the system according to an aspect of the disclosure. This calibration can be implemented in different ways, for example by determining the brightness of the light sources 8 and an adjustment to an identical value for light sources 8. To this end it is possible, in particular, to steer the light from the light sources 8 to the detector 2 with a surface and to set the brightness of at least one light source 8 in such a way that the detector 2 detects the same intensity when the light sources 8 are switched on alternately. During this calibration it is important that the light from the light sources 8 strikes the surface at the same angle.

Furthermore, there is the option within the operation of the system according to an aspect of the disclosure of carrying out a calibration of the light sources 8. This will be explained on the basis of FIG. 8.

Figure 8:
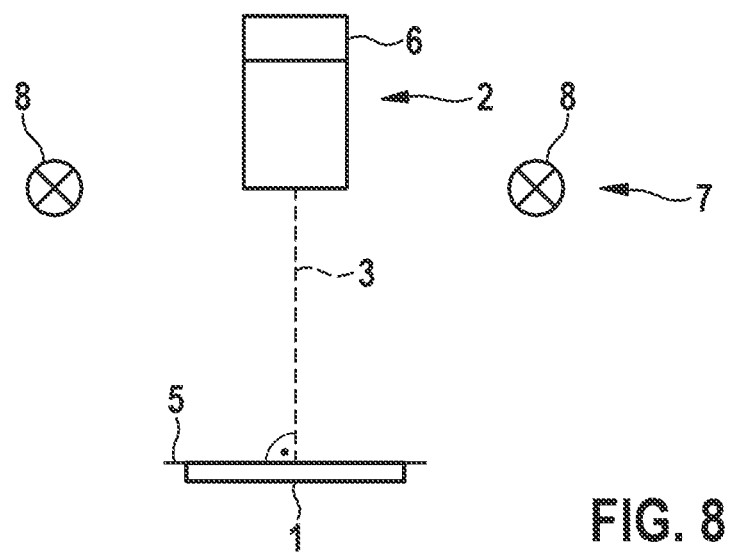
FIG. 8 shows a schematic side view of the system during the calibration of the light sources according to the first exemplary embodiment of the disclosure.

FIG. 8 shows a schematic side view of the system during the calibration of the light sources 8 according to the first exemplary embodiment of the disclosure.

As is evident from FIG. 8, the marker 1 is arranged centrally with respect to the optical axis 3 of the detector 2 and is oriented such that it is oriented perpendicular to the optical axis 3 of the detector 2 or parallel to the plane 5. Expressed differently, the marker 1 is not tilted. The accuracy of the calibration depends on the accuracy of the positioning and the orientation of the marker 1. Then, one of the two light sources 8 is initially put into operation, for example the light source 8 depicted to the left in FIG. 8, and the intensity of the light steered from the marker 1 to the detector 2 is detected with the aid of the detector 2. Subsequently, the switched-on light source 8 is switched off again and, instead, the other light source 8 is put into operation, for example the light source 8 depicted to the right in FIG. 8, and the intensity of the light steered from the marker 1 to the detector 2 is detected again with the aid of the detector 2. This intensity value is compared to the intensity value determined first and the brightness of the switched-on light source 8 is varied while the intensity is continually detected until the current intensity value corresponds to the intensity value determined first. This completes the calibration. The brightness set thus is maintained for the subsequent determination of the relative spatial position of the marker 1. To this end, it is necessary to ensure that, following a switch off and a subsequent switch on, the brightness of the light source 8 set during the calibration is obtained again.

In the first exemplary embodiment, the tilt axis 4 of the marker 1 is oriented perpendicular to a connecting line between the two light sources 8. As a result, the maximum difference between the angles of incidence of the light of the two light sources 8 on the marker 1, and hence the maximum difference in the detected intensity for the two light sources 8, arises for a given tilt of the marker 1. However, the marker 1 employed in the process may adopt very different relative spatial positions depending on the type of medical examination or medical intervention, and so the difference between the angles of incidence of the light of the two light sources 8 on the marker 1, and hence the difference in the intensity detected for the two light sources 8, may be very small. Should the tilt axis 4 of the marker 1 randomly be oriented parallel to the connecting line between the two light sources 8, the difference between the angles of incidence may even completely disappear, and so no intensity difference is determinable anymore and hence it is no longer possible to make a statement in respect of the direction of the tilt.

Such a situation may be avoided if use is made of more than two light sources 8 which are not arranged on a straight line. The more light sources 8 are present, the larger the chance that these include two opposing light sources 8 whose connecting line is oriented virtually perpendicular to the tilt axis 4 of the marker 1. Typically, use is made of an even number of light sources 8 so that there is the option of in each case switching on exactly half of the light sources 8 and switching off the other half of the light sources 8. A second exemplary embodiment of the system according to the disclosure comprising four light sources 8 is described below.

Figure 9:
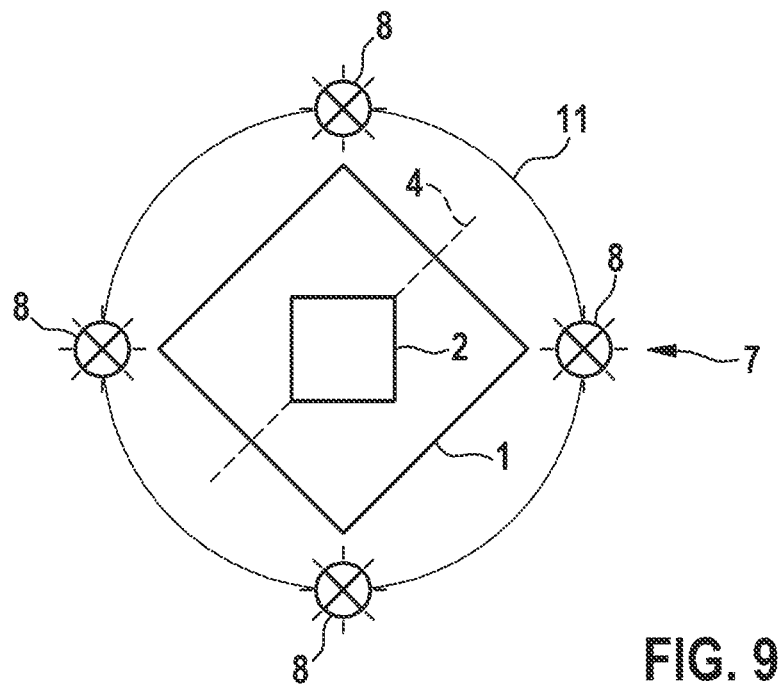
FIG. 9 shows a schematic plan view of the system during a first operational state according to a second exemplary embodiment of the disclosure.

FIG. 9 shows a schematic plan view of the system during a first operational state according to a second exemplary embodiment of the disclosure.

Four light sources 8 are provided in the second exemplary embodiment and are arranged on a circle 11 that is concentric with the optical axis 3 of the detector 2. The light sources 8 are arranged equidistantly from one another, that is to say two adjacent light sources 8 in each case include a center angle of 90°. To keep the complexity manageable, a geometry, an exemplary embodiment of which is shown in FIG. 12, in which the marker 1 is tilted about one tilt axis 4 only was chosen for the representation. However, it is likewise possible for the marker 1 to be tilted about two tilt axes 4 or to include other geometry elements.

By evaluating the image information in the pattern 10 of the marker 1 detected by the detector 2 while taking account of the known dimensions of the pattern 10 and the optical properties of the detector 2, all spatial and angle coordinates of the marker 1 are determined first, with the orientation of the tilt axis 4 and the absolute value of the tilt angle α, but not the direction of the tilt, being determined for said tilt. To this end, all light sources 8 may be switched off or switched on, depending on the ambient illumination. All light sources 8 are switched on in the representation of FIG. 9.

The direction of the tilt is determined in a next step by evaluating the luminous intensity when illuminating the marker 1 from different directions. This will be explained on the basis of FIGS. 10 and 11.

Figure 10:
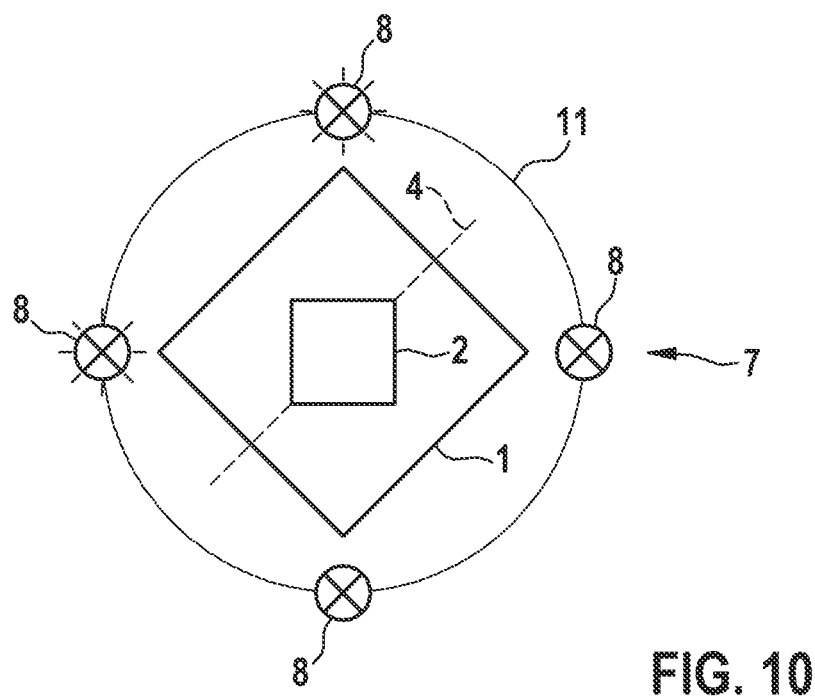
FIG. 10 shows a schematic side view of the system during a second operational state according to the second exemplary embodiment of the disclosure.

FIG. 10 shows a schematic side view of the system during a second operational state according to the second exemplary embodiment of the disclosure.

During the second operational state, the light sources 8 are actuated by the evaluation device 6 in such a way that all light sources 8 on one side of the tilt axis 4 are switched on and all light sources 8 on the other side of the tilt axis 4 are switched off. In the representation of FIG. 10, the left and top light source 8 are switched on and the right and bottom light source 8 are switched off. The relative position of the tilt axis 4 is known to the evaluation device 6 as a result of the measurement carried out in the first operational state. In a manner analogous to what was described for the first exemplary embodiment, the detector 2 detects the intensity of the light of the switched-on light sources 8 steered from the marker 1 to the detector 2 and transmits the detected value to the evaluation device 6. Subsequently, a further measurement is carried out in a third operational state.

Figure 11:
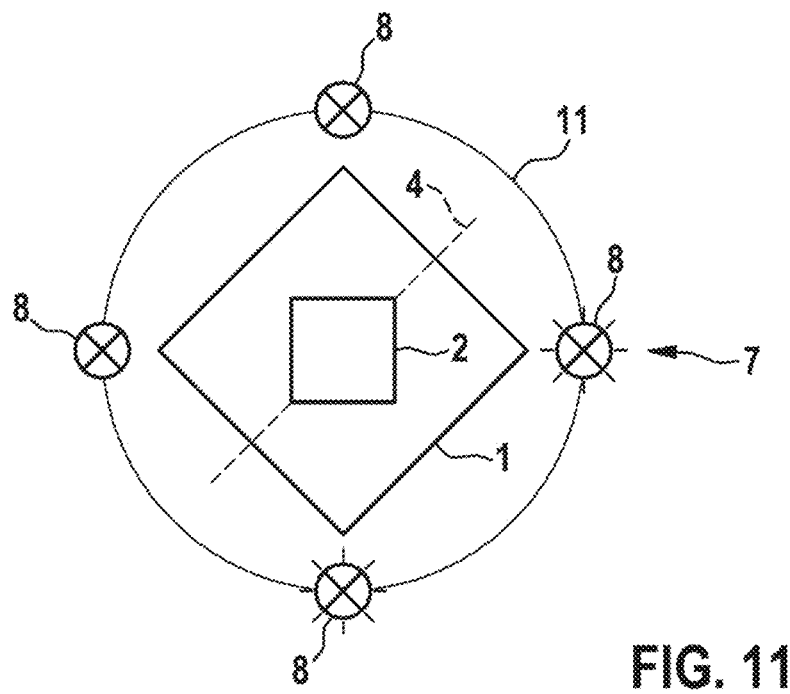
FIG. 11 shows a schematic side view of the system during a third operational state according to the second exemplary embodiment of the disclosure.

FIG. 11 shows a schematic side view of the system during a third operational state according to the second exemplary embodiment of the disclosure.

During the third operational state, the light sources 8 are actuated by the evaluation device 6 in such a way that the previously switched-on light sources 8 are switched off and the previously switched-off light sources 8 are switched on. Accordingly, the light sources 8 which are switched on now are on the other side of the tilt axis 4 to those switched on in the second operational state. In the representation of FIG. 11, the right and bottom light source 8 are switched on and the left and top light source 8 are switched off. In a manner analogous to what was described for the first exemplary embodiment, the detector 2 detects the intensity of the light of the switched-on light sources 8 steered from the marker 1 to the detector 2 and transmits the detected value to the evaluation device 6. The evaluation device 6 analyses the intensity values detected during the second and during the third operational state and, in the manner analogous to what was described for the first exemplary embodiment, determines the direction of the tilt therefrom.

The remarks made in relation to the first exemplary embodiment regarding the need to ensure identical conditions during the detection of the luminous intensity in the second and third operational state, regarding the calibration of the light sources 8, etc., apply analogously to the second exemplary embodiment and to further exemplary embodiments with a deviating number of light sources 8.

In all exemplary embodiments there is the option of realizing the various operational states not by switching the light sources 8 on and off but by leaving the light sources 8 switched on permanently and selectively blocking and clearing the light path to the marker 1 with upstream stops.

It is likewise also possible to use a plurality of light sources 8 which are permanently switched on independently of the operational state, with a first subset of light sources 8 emitting light at a first wavelength and a second subset of light sources 8 emitting light at a second wavelength. A selective detection of the light from the first or the second subset of light sources 8 is possible by switching the detector 2 over to a detection of the first wavelength or the second wavelength. This switchover may also be implemented with filters placed in front of the detector 2. When use is made of a detector 2 in the form of an RGB camera, a wavelength-selective detection is realizable particularly easily since separate signals for the detected light at different wavelengths are output in any case without additional measures. By way of example, a respective signal is output for the detection of red, green, and blue light. Thus, all that is necessary is to provide a first subset of light sources 8 which emit for example red light and a second subset of light sources 8 which emit for example green light or blue light. Then, there is the option of respectively separately registering and evaluating the light originating from the light sources 8 of the two subsets without additional outlay despite the simultaneous irradiation by the light sources 8 of both subsets. In this case, there is no need to switch over the detector 2 as it can register the light of different colors in parallel.

In a further variant, the illumination device 7 has a movable light source 8 and the same light source 8 is sequentially arranged at the various positions in this variant, instead of a sequential operation of a plurality of light sources 8 arranged in stationary fashion at different positions. In this case, the light source 8 may remain permanently in operation if this does not impede the detection by the detector 2. By way of example, the detector 2 may be controlled in such a way that a detection only ever occurs if the light source 8 is at one of the envisaged positions. As a result, intermediate positions can be masked. It is likewise also possible to switch the movable light source 8 on and off. Compared to a plurality of light sources 8, this makes it possible to easily ensure the same brightness at all times, rendering a calibration superfluous.

In all exemplary embodiments, it is possible to vary the brightness of the light sources 8 depending on the spatial position of the marker 1. By way of example, it is possible to vary the brightness of the light sources 8 depending on the distance between the light sources 8 and the marker 1 and/or between the marker 1 and the detector 2. In particular, it is possible to choose a high brightness in the case of a long distance and a low brightness in the case of a short distance. As a result, it is possible to ensure sufficient illumination in the case of long distances and at the same time prevent an overexposure at short distances. In the process, it is not only possible to regulate the brightness of all switched-on light sources 8 together. Individual regulation is likewise possible, for example if the marker 1 is displaced transversely to the optical axis 3 of the detector 2 and hence has different distances from the individual light sources 8. Then, by way of compensation, the light sources 8 that are further away from the marker 1 can be operated at a higher brightness than the light sources 8 arranged closer to the marker 1.

The utilized light sources 8 may each have an insubstantial directional characteristic and emit light of the same intensity over a large solid angle range, in particular within the solid angle range provided for the illumination of the marker 1, and hence have an isotropic emission characteristic for this solid angle range. What this can achieve is that the illumination of the marker 1 depends predominantly on the distance to the light source 8 and depends less strongly on the relative positioning.

The disclosure may possibly also be adapted for use in coordinate measuring machines.

To obtain a higher accuracy, the symmetry of the scattering function according to which the marker 1 deflects the incident light may be broken in relation to the normal oriented perpendicular to the marker 1. By way of example, this may be realized by virtue of sawtooth profiles or other surface inclinations that differ between surface segments being formed on the surface of the marker 1. The sawtooth profiles may have varying amplitudes and angles of inclination. Moreover, the inclination of the sawtooth profiles on the surface of the marker 1 may be formed along different directions within the plane of the surface, wherein all directions may occur in approximately equally distributed fashion. By way of example, the sawtooth profiles may each extend like rays in all directions within the plane of the surface, starting from a central point on the surface of the marker 1. It is likewise also possible to form other surface segments with different surface inclinations, in particular with equally distributed surface inclinations. To this end, use can also be made of methods that produce a statistical distribution of surface inclinations. The distribution of the surface inclinations can be taken into account when evaluating the intensity, registered by the detector, for determining the tilt direction of the marker 1. In the process, it is possible to obtain even more precise results if it is not just the intensity accumulated over the entire detector surface but also image information, that is to say the intensity distribution, that is evaluated.

Furthermore, the symmetry of the arrangement of the light sources 8 relative to the optical axis 3 of the detector 2 can be broken. By way of example, this can be achieved by virtue of the fact that no concentric arrangement of the light sources 8 about the optical axis 3 of the detector 2 is chosen.

Moreover or alternatively, the light sources 8 may be formed in such a way that they do not have an isotropic emission characteristic but instead are intensity modulated in a direction-dependent fashion, that is to say radiate with different intensities in different directions. This likewise represents a measure for increasing the resolution when determining the tilt direction of the marker 1 and has a particular effect should the distances between the marker 1 and the light sources 8 be large and/or the distances of the light sources 8 from the optical axis 3 be small. In the case of such set-ups, the angles of incidence on the marker 1 of the light from the individual light sources 8 only differ slightly. By arranging suitable optical elements in the beam path of the light sources 8, it is possible to design the direction-dependent intensity modulation in such a way that the marker 1 is illuminated over the whole area with light that has the same angle distribution.

To the extent that this is possible for reasons of space, the light sources 8 may be arranged at the largest possible distances from the optical axis 3 of the detector 2 in order to obtain the largest possible variation in the angles of incidence on the marker 1 of the light from the individual light sources 8.

The resolution when determining the tilt direction of the marker 1 may also be increased by virtue of a rolling shutter camera being used as a detector 2, in the case of which the image information is read line-by-line or column-by-column and the light sources 8 are actuated in such a way that they emit a time-modulated luminous intensity. The known sequence of the camera readout and the known modulation of the luminous intensity are taken into account during the evaluation of the detector signals. Although this leads to an increased computational outlay, this also provides an increased resolution.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Marker
2 Detector
3 Optical axis
4 Tilt axis
5 Plane
6 Evaluation device
7 Illumination device
8 Light source
9 Carrier
10 Pattern
11 Circle

What is claimed is:

1. A medical apparatus for determining a relative spatial position of a planar marker, the medical apparatus comprising:
 an illumination device configured to illuminate the planar marker with light;
 a detector defining an optical axis and being configured to detect the light reflected from the planar marker to the detector; and
 an evaluation device configured to determine a direction of a tilt of the planar marker relative to a plane oriented perpendicular to the optical axis from an analysis of a first value detected by the detector while the planar marker is illuminated from a first direction and a second value detected by the detector while the planar marker is illuminated from a second direction,
 wherein the first value is a first luminous intensity value and the second value is a second luminous intensity value and each of the first and second values is detected in a different operational state of the illumination device.

2. The medical apparatus according to claim 1, wherein the first direction and the second direction from which the planar marker is illuminated are varied depending on a spatial orientation of a tilt axis about which the planar marker is tilted.

3. The medical apparatus according to claim 1, wherein an illumination of the planar marker is varied depending on the relative spatial position of the planar marker.

4. The medical apparatus according to claim 1, wherein the illumination device illuminates the planar marker with the light at a different wavelength to ambient light in operational surroundings provided for the medical apparatus.

5. The medical apparatus according to claim 1, wherein the illumination device has a plurality of light sources and an illumination from the first direction is realized by a first subset of light sources and the illumination from the second direction is realized by a second subset of light sources.

6. The medical apparatus according to claim 5, wherein the light sources have at least in pairs an identical emission characteristic within a solid angle range provided for the illumination of the planar marker.

7. The medical apparatus according to claim 5, wherein the first subset of light sources and the second subset of light sources are switched on and off in a complementary fashion to switch between the illumination from the first direction and the illumination from the second direction.

8. The medical apparatus according to claim 5, wherein the first subset of light sources emits light at a first wavelength and the second subset of light sources emits light at a second wavelength.

9. The medical apparatus according to claim 8, wherein the first value is detectable by detecting light at the first wavelength and the second value is detectable by detecting light at the second wavelength.

10. The medical apparatus according to claim 5, wherein the illumination device has an even number of light sources.

11. The medical apparatus according to claim 5, wherein the illumination device has more than two light sources.

12. The medical apparatus according to claim 5, wherein the light sources are arranged on a circle that is concentric with an optical axis of the detector.

13. The medical apparatus according to claim 1, wherein the detector is a camera.

14. The medical apparatus according to claim 1, wherein the medical apparatus is a surgical microscope.

15. A system, comprising:
 the medical apparatus according to claim 1; and
 the planar marker.

16. The system according to claim 15, wherein the planar marker has a geometric pattern.

17. The planar marker according to claim 16, wherein the geometric pattern is a quick response code.

18. A method for determining a relative spatial position of a planar marker, the method comprising:
- providing a detector defining an optical axis and being configured to detect light reflected from the planar marker to the detector;
- illuminating the planar marker from a first direction and detecting a first value by the detector;
- illuminating the planar marker from a second direction and detecting a second value by the detector; and
- determining a direction of a tilt of the planar marker relative to a plane oriented perpendicular to the optical axis from the first value and the second value,
- wherein the first value is a first luminous intensity value, and the second value is a second luminous intensity value and each of the first and second values is detected in a different operational state of the illumination device.

* * * * *

UNITED STATES PATENT AND TRADEMARK OFFICE
CERTIFICATE OF CORRECTION

PATENT NO. : 12,369,989 B2
APPLICATION NO. : 17/705238
DATED : July 29, 2025
INVENTOR(S) : Christian Voigt and Nils Haverkamp It is certified that error appears in the above-identified patent and that said Letters Patent is hereby corrected as shown below:

On the Title Page

Item (56) U.S. PATENT DOCUMENTS:

Replace "5,038,258 A 8/1991 Koch" with "5,038,258 A 8/1991 Koch et al."

Replace "8,988,505 B2 3/2015 Schaerer" with "8,988,505 B2 3/2015 Schaerer et al."

Replace "10,314,490 B2 6/2019 Ntziachristos" with "10,314,490 B2 6/2019 Ntziachristos et al."

Replace "2002/0040190 A1 4/2002 Nagele" with "2002/0040190 A1 4/2002 Nagele et al."

Replace "2008/0103390 A1 5/2008 Contag" with "2008/0103390 A1 5/2008 Contag et al."

Replace "2016/0228198 A1 8/2016 Hong" with "2016/0228198 A1 8/2016 Hong et al."

Replace "2017/0143442 A1 5/2017 Tesar" with "2017/0143442 A1 5/2017 Tesar et al."

Replace "2019/0328464 A1 10/2019 Saur" with "2019/0328464 A1 10/2019 Saur et al."

Signed and Sealed this
Twenty-third Day of September, 2025

John A. Squires
*Director of the United States Patent and Trademark Office*